US005674477A

United States Patent [19]
Ahluwalia

[11] Patent Number: 5,674,477
[45] Date of Patent: Oct. 7, 1997

[54] REDUCTION OF HAIR GROWTH

[76] Inventor: Gurpreet S. Ahluwalia, 8632 Stable View Ct., Gaithersburg, Md. 20879

[21] Appl. No.: 396,426

[22] Filed: Feb. 28, 1995

[51] Int. Cl.$^6$ ................................................. A61K 7/06
[52] U.S. Cl. .................. 424/70.1; 424/401; 514/456; 514/880
[58] Field of Search ................................ 424/400, 401, 424/73, 70.1, 40; 514/880, 456

[56] References Cited

U.S. PATENT DOCUMENTS

| | | | |
|---|---|---|---|
| 3,426,137 | 2/1969 | Philpitt et al. | 424/401 |
| 4,039,669 | 8/1977 | Beyler et al. | 424/401 |
| 4,139,638 | 2/1979 | Neri et al. | 424/401 |
| 4,161,540 | 7/1979 | Neri et al. | 424/401 |
| 4,191,775 | 3/1980 | Glen | 260/562 |
| 4,269,831 | 5/1981 | Ferrari et al. | 424/401 |
| 4,344,941 | 8/1982 | Wiechert et al. | 424/401 |
| 4,370,315 | 1/1983 | Greff et al. | 424/73 |
| 4,439,432 | 3/1984 | Peat | 424/401 |
| 4,508,714 | 4/1985 | Cecic et al. | 424/400 |
| 4,517,175 | 5/1985 | Iwabuchi et al. | 424/70 |
| 4,720,489 | 1/1988 | Shander | 514/171 |
| 4,885,289 | 12/1989 | Breuer et al. | 514/170 |
| 4,935,231 | 6/1990 | Pigiet | 424/71 |
| 5,095,007 | 3/1992 | Ahluwalia | 514/23 |
| 5,096,911 | 3/1992 | Ahluwalia et al. | 514/380 |
| 5,132,293 | 7/1992 | Shander et al. | 514/46 |
| 5,143,925 | 9/1992 | Shander et al. | 514/378 |
| 5,189,212 | 2/1993 | Ruenitz | 562/468 |
| 5,271,942 | 12/1993 | Heverhagen | 424/74 |
| 5,300,284 | 4/1994 | Wiechers et al. | 424/401 |
| 5,364,885 | 11/1994 | Ahluwalia et al. | 514/563 |
| 5,411,991 | 5/1995 | Shander et al. | 514/665 |

FOREIGN PATENT DOCUMENTS

| | | |
|---|---|---|
| 1 458 349 | 12/1976 | European Pat. Off. . |
| 0 413 528 A1 | 2/1991 | European Pat. Off. . |
| 0 532 219 A2 | 3/1993 | European Pat. Off. . |
| 59-187097 | 10/1984 | Japan . |
| 5301821 | 11/1992 | Japan . |
| 5301821 | 11/1993 | Japan . |
| 6009391 | 1/1994 | Japan . |
| 9210245 | 11/1992 | Rep. of Korea . |
| 9308763 | 9/1993 | Rep. of Korea . |
| 9324106-A | 12/1993 | WIPO . |
| 9414414 | 8/1994 | WIPO . |

OTHER PUBLICATIONS

Notification of Transmittal of the International Search Report or the Declaration (7 pages).
FR 2527927 (Dec. 9, 1983) Abstract.
FR 2708851 (Feb. 17, 1995) Abstract.
Harmon et al., "12–O–Tetradecanoylphorbol–13–Acetate Inhibits Human Hair Follicle Growth and Hair Fiber Production in Whole–Organ Cultures", *SID Abstracts*, 102:553 (Apr., 1994).
Simpson et al., "The effect of topically applied progesterone on sebum excretion rate", *British Journal of Dermatology*, 100:687–692 (1979).
Messenger, "The Control of Hair Growth: An Overview", *Journal of Investigative Dermatology*, 101:4S–9S (Jul., 1993).
Sato, "The Hair Cycle and its Control Mechanism", *Biology and Disease of the Hair*, 3–13 (1975).
Lunder, "Catechins of Green Tea: Antioxidant Activity", *Phenolic Compounds in Food and Their Effects on Health II*, Chapter 9, pp. 114–120 (1992).
Mukhtar et al., "Green Tea and Skin —Anticarcinogenic Effects", *The Journal of Investigative Dermatology*, 102:3–7 (1994).
Katiyar et al., "Inhibition of 12–O–Tetradecanoylphorbol–13–acetate–caused Tumor Promotion in 7,12–Dimethylbenz [a]anthracene–initiated . . . ", *Cancer Research*, 52:6890–6897 (1992).
Agarwal et al., "Inhibition of Skin Tumor Promoter–caused Induction of Epidermal Ornithine . . . ", *Cancer Research*, 52:3582–3588 (1992).
CA113(15):126168f of Hear. Res. 46(1–2), 101–12 (1990).
Burdick et al., "The Topical Effect of the Antiandrogen Chlormadin —One Acetate and Some of its . . . ", *Br. J. Derm.*, 82:19–25, Supplement 6, 19 (1970).
Goos et al., "An Improved Method for Evaluating Antiandrogens", *Arch. Dermatol. Res.*, 273:333–341 (1982).

*Primary Examiner*—Jyothsan Venkat
*Attorney, Agent, or Firm*—Fish & Richardson P.C.

[57] ABSTRACT

Mammalian hair growth is reduced by applying to the skin a dermatologically acceptable composition including a catechin compound.

21 Claims, No Drawings

REDUCTION OF HAIR GROWTH

The invention relates to a method of reducing unwanted hair growth in mammals.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic anti-androgens. These conventional procedures generally have drawbacks associated with them. Shaving, for instance, can cause nicks and cuts and can also promote the perception of an increase in the rate of hair regrowth. Shaving also can leave stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

Green tea is a common beverage consumed throughout the world, particularly in Asian countries. The tea leaves contain such chemically active components as flavanols, flavonoids, and phenolic acids. These components may represent as much as ⅓ the dry weight of green tea leaves. The catechins present in the leaves are from the chemical class polyphenols. Four major catechins have been isolated from the leaves: epicatechin, epicatechin gallate, epigallocatechin, and epigallocatechin gallate.

It has now been found that unwanted mammalian (including human) hair growth—particularly androgen-stimulated hair growth—can be reduced by applying to the skin a dermatologically acceptable composition including a catechin compound in an amount effective to reduce hair growth. The unwanted hair growth which is reduced may be normal hair growth, or hair growth that results from an abnormal or diseased condition. The preferred catechin compounds are the four major catechin compounds present in green tea leaves.

A "catechin compound", as used herein, is a compound that includes the following ring structure

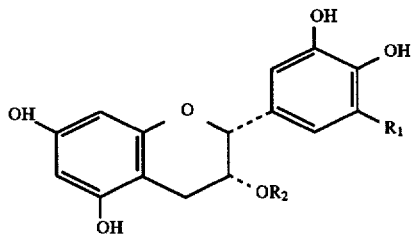

For (—)-epicatechin (EC), $R_1$ and $R_2$ are H. For (—)-epicatechin gallate (ECG), $R_1$ is H and $R_2$ is

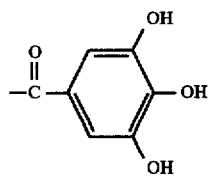

For (—)-epigallocatechin (EGC), $R_1$ is OH and $R_2$ is H. And for (—)-epigallocatechin gallate (EGCG), $R_1$ is OH and $R_2$ is the same as in (—)-epicatechin gallate (ECG). Other catechin compounds include afzelchin, gallocatechin, catechin oligomers (procyanidins), and oxidative dimers of catechin (theaflavin, theaflavin monogallate, theaflavin digallate). In addition, "catechin compound", as used herein, encompasses compounds in which one or more of the hydroxy groups in the above ring structure are replaced by ester groups (e.g., alkyl esters such as methyl and ethyl esteric).

Epicatechin, epicatechin gallate, epigallocatechin, epigallocatechin gallate were isolated from green tea leaves according to the procedure described by R. Agarwal et al., Cancer Research 52:3582–3588 (1992), with some modification. Dried green tea leaves were extracted with hot water at 80° C. under nitrogen. The hot water extraction was repeated twice. The residual leaves were further extracted with 80% ethanol by gently agitating at 25°–30° C. on a horizontal shaker at 125 rpm for 1 hr. The water and the ethanol extracts were combined. The hydro-alcoholic (water-ethanol) extract was treated with chloroform to remove caffeine and pigments. The chloroform layer was separated from the hydro-alcoholic layer using a separatory funnel. The latter fraction was extracted three times under nitrogen with ethyl acetate. The ethyl acetate layer was separated and subjected to rotary evaporation to remove the organic solvent. The residue was dissolved in water and freeze-dried. This resulted in an off-white to slightly yellow dried residue of green tea polyphenols (GTP). The total yield of the polyphenolic fraction was 10.3%. The percent composition of individual polyphenol component in the mixture was determined on a reverse-phase HPLC system. The HPLC analysis revealed four major catechin components in the mixture: epigallocatechin (4.6%), epigallocatechin gallate (69.6%), epicatechin (6.7%) and epicatechin gallate (19.1%).

The individual catechin components were further purified on a preparative reverse phase HPLC system. The freeze-dried GTP's fraction was dissolved in water, and loaded on to a 40×300 mm C-18 reverse phase column. The catechin compounds were eluted from the column using a gradient elution with water (adjusted to pH 4.4 with formic acid) and ethanol. The column eluent was collected at 1 min intervals. HPLC fractions containing purified epigallocatechin, epigallocatechin gallate, epicatechin, and epicatechin gallate (as verified using analytical reverse phase system) were pooled and freeze-dried.

The catechin compound preferably is incorporated in a topical composition which includes a non-toxic dermatologically acceptable vehicle or carrier which is adapted to be spread upon the skin. Examples of suitable vehicles are acetone, alcohols, or a cream, lotion, or gel which can effectively deliver the active compound. One such vehicle is disclosed in co-pending application PCT/US 93/0506A. In addition, a penetration enhancer may be added to the vehicle to further enhance the effectiveness of the formulation.

The concentration of the catechin compound in the composition may be varied over a wide range up to a saturated solution, preferably from 0.1% to 40% by weight or even more; the reduction of hair growth increases as the amount of the catechin compound applied increases per unit area of skin. A catechin compound can be used in purified form or as a mixture; for example the mixture of catechin compounds isolated from green tea leaves as previously described can be used without further purification. The maximum amount effectively applied is limited only by the rate at which the catechin compound penetrates the skin. Generally, the effective amounts range from 100 to 3000 micrograms or more per square centimeter of skin.

The composition should be topically applied to a selected area of the body from which it is desired to reduce hair growth. For example, the composition can be applied to the face, particularly to the beard area of the face, i.e., the cheek, neck, upper lip, and chin. The composition can also be applied to the legs, arms, torso or armpits. The composition is particularly suitable for reducing the growth of unwanted hair in women suffering from hirsutism or other conditions. In humans, the composition should be applied once or twice a day, or even more frequently, for at least three months to achieve a perceived reduction in hair growth. Reduction in hair growth is demonstrated when the frequency of hair removal (shaving, tweezing, depilatory use, waxing) is reduced, or the subject perceives less hair on the treated site, or quantitatively, when the weight of hair removed by shaving (i.e., hair mass) is reduced. Benefits of reduced hair removal frequency include convenience and less skin irritation.

Male intact Golden Syrian hamsters are considered acceptable models for human beard hair growth in that they display oval shaped flank organs, one on each side, each about 8 mm. in major diameter, which grow thick black and coarse hair similar to human beard hair. These organs produce hair in response to androgens in the hamster. To evaluate the effectiveness of a particular catechin compound, or mixture of catechin compound, the flank organs of each of a group of hamsters are depilated by applying a thioglycolate based chemical depilatory (Surgex). To one organ of each animal 10–25 μL. of vehicle alone once a day is applied, while to the other organ of each animal an equal amount of vehicle containing a catechin compound is applied. After thirteen applications (one application per day for five days a week), the flank organs are shaved and the amount of recovered hair (hair mass) from each is weighed. Percent-reduction of hair growth is calculated by subtracting the hair mass (mg) value of the test compound treated side from the hair mass value of the vehicle treated side; the delta value obtained is then divided by the hair mass value of the vehicle treated side, and the resultant number is multiplied by 100.

The above-described assay will be referred to herein as the "Golden Syrian hamster" assay. Preferred compositions provide a reduction in hair growth of at least about 35%, more preferably at least about 50%, and most preferably at least about 70% when tested in the Golden Syrian hamster assay.

The mixture of catechins isolated from green tea leaves as described previously were tested in the Golden Syrian hamster assay. The mixture caused a dose dependent reduction of hair growth in the range of 46–91%. The mixture was tested at a 5, 10, 20 and 30% dose. The results are presented in Table 1.

TABLE I

Reduction of Hair Growth Using Mixture of Catechin Compounds

| Treatment | Vehicle | Dose | pH | Untreated | Treated | % Inhibition |
|---|---|---|---|---|---|---|
| Mixture | A[1] | 5% | 5.0 | 2.29 ± .21 | 1.25 ± .17 | 46 ± 7 |
| Mixture | A | 10% | 4.5 | 2.21 ± .17 | 0.58 ± .11 | 73 ± 5 |
| Mixture | A | 20% | 5.0 | 2.84 ± .21 | 0.42 ± .10 | 85 ± 4 |
| Mixture | A | 30% | 5.0 | 2.34 ± .21 | 0.25 ± .13 | 91 ± 5 |
| Control | A | NA[2] | 4.6 | 2.20 ± .18 | 2.35 ± .20 | NI[3] |

[1]Vehicle A: Pure water (68%), ethanol (16%), propylene glycol (5%), dipropylene glycol (5%), benzyl alcohol (4%) and propylene carbonate (2%)
[2]NA: Not applicable
[3]NI: No inhibition Epigallocatechin (EGC), epigallocatechin gallate (EGCG), epicatechin (EC), and epicatechin gallate (ECG), purified as described previously, also were tested in a Golden Syrian hamster assay. The results are presented in Table 2. Among the four catechins, epigallocatechin gallate was found to be the most potent. The hair growth reductions ranged from 58 to 81%. In a dose response study, this compound was found to be quite effective even at a 1% concentration, which produced a 53% hair growth reduction.

TABLE 2

Reduction of Hair Growth by Purified Catechin Compounds

| Treatment | Vehicle | Dose | pH | Untreated | Treated | % Inhibition |
|---|---|---|---|---|---|---|
| EGCG | A[1] | 1% | 3.5 | 2.74 ± .30 | 1.26 ± .12 | 53 ± 47 |
| EGCG | A | 2.5% | 3.5 | 2.32 ± .09 | 0.98 ± .14 | 58 ± 6 |
| EGCG | A | 5% | 3.5 | 2.16 ± .30 | 0.45 ± .11 | 67 ± 15 |
| EGCG | A | 10% | 3.5 | 2.62 ± .24 | 0.45 ± .25 | 81 ± 11 |
| ECG | A | 10% | 4.5 | 2.94 ± .50 | 0.64 ± .14 | 73 ± 7 |
| EGC | A | 10% | 3.5 | 2.15 ± .33 | 0.57 ± .17 | 65 ± 12 |
| EC | A | 10% | 3.5 | 1.94 ± .25 | 0.74 ± .17 | 58 ± 9 |
| Control | A | NA[2] | 4.0 | 2.39 ± .21 | 2.44 ± .38 | NI[3] |

[1]Vehicle A: Pure water (68%), ethanol (16%), propylene glycol (5%), dipropylene glycol (5%), benzyl alcohol (4%) and propylene carbonate (2%)
[2]NA: Not applicable
[3]NI: No inhibition It will be appreciated by those skilled in the art that the invention can be performed within a wide range of equivalent parameters of composition and conditions without departing from the spirit or scope of the invention or of any embodiment thereof.

I claim:

1. A method of reducing mammalian hair growth, comprising
    selecting an area of skin from which reduced hair growth is desired; and
    applying to said area of skin a dermatologically acceptable composition including a catechin compound in an amount effective to reduce hair growth, said catechin compound having the following structure

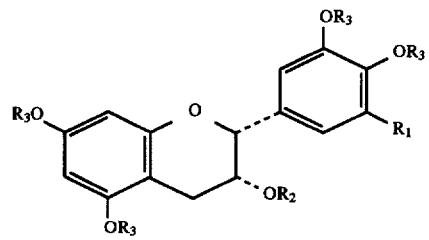

wherein $R_1$ is —H or —OH, $R_2$ is H or

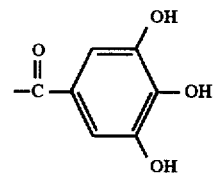

and each $R_3$, independently, is —H,

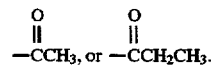

2. The method of claim 1, wherein said catechin compound is epigallocatechin gallate.

3. The method of claim 1, wherein said catechin compound is epicatechin gallate.

4. The method of claim 1, wherein said catechin compound is epigallocatechin.

5. The method of claim 1, wherein said catechin compound is epicatechin.

6. The method of claim 1, wherein said composition includes a mixture of catechin compounds.

7. The method of claim 6, wherein said mixture of catechin compounds are derived from green tea leaves.

8. The method of claim 1, wherein the concentration of said catechin compound in said composition is between 1% and 40%.

9. The method of claim 1, wherein the composition is applied to the skin in an amount of from 100 to 4000 micrograms of said catechin compound per square centimeter of skin.

10. The method of claim 1, wherein the composition is applied to the skin on the face of said mammal.

11. The method of claim 1, wherein the composition provides a reduction in hair growth of at least 30% when tested in the Golden Syrian hamster assay.

12. The method of claim 1, wherein the composition provides a reduction in hair growth of at least 50% when tested in the Golden Syrian hamster assay.

13. The method of claim 1, wherein the composition provides a reduction in hair growth of at least 70% when tested in the Golden Syrian hamster assay.

14. The method of claim 1, wherein said mammal is a human.

15. The method of claim 1, wherein said area of skin comprises an area suffering from hirsutism.

16. The method of claim 1, wherein said composition further comprises a non-toxic, dermatologically acceptable carrier or vehicle.

17. A method of reducing mammalian hair growth, comprising selecting an area of skin from which reduced hair growth is desired; and applying to said area of skin a dermatologically acceptable composition comprising a catechin compound selected from the group consisting of epigallocatechin gallate, epicatechin gallate, epigallocatechin, epicatechin, afzelchin, gallocatechin, procyanidins, theaflavin, theaflavin monogallate, and theaflavin digallate, in an amount effective reduce hair growth.

18. The method of claim 17, wherein the composition is applied to the skin on the face of said mammal.

19. The method of claim 17, wherein the composition provides a reduction in hair growth of at least 30% when tested in the Golden Syrian hamster assay.

20. The method of claim 17, wherein said mammal is human.

21. The method of claim 17, wherein said area of skin comprises an area suffering from hirsutism.

* * * * *